United States Patent
Melman et al.

(10) Patent No.: US 6,404,495 B1
(45) Date of Patent: *Jun. 11, 2002

(54) SYSTEM AND METHOD FOR MOLECULAR SAMPLE MEASUREMENT

(75) Inventors: Paul Melman, Newton; Marvin Tabasky, Peabody, both of MA (US)

(73) Assignee: Corning Applied Technologies Corporation, Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/546,058

(22) Filed: Apr. 10, 2000

Related U.S. Application Data

(60) Division of application No. 09/345,904, filed on Jul. 1, 1999, which is a continuation-in-part of application No. 09/010,031, filed on Jan. 21, 1998, now Pat. No. 6,084,667, which is a continuation-in-part of application No. 08/815,219, filed on Mar. 12, 1997, now Pat. No. 5,903,348.

(51) Int. Cl.[7] .............................................. G01N 21/00
(52) U.S. Cl. ...................................... 356/344; 204/451
(58) Field of Search ................................ 356/344, 244, 356/246; 204/451, 452, 455, 470, 601, 603, 605, 619, 620, 612

(56) References Cited

U.S. PATENT DOCUMENTS

| | | | |
|---|---|---|---|
| 4,639,074 A | 1/1987 | Murphy | 350/96.15 |
| 4,729,947 A | 3/1988 | Middendorf et al. | 435/6 |
| 4,927,265 A | 5/1990 | Brownlee | 356/73 |
| 5,114,551 A | 5/1992 | Hjerten et al. | 204/180 |
| 5,274,240 A | 12/1993 | Mathies et al. | 250/458 |
| 5,312,535 A | 5/1994 | Waska et al. | 204/299 |
| 5,324,401 A | 6/1994 | Yeung et al. | 204/180 |
| 5,359,686 A | 10/1994 | Galloway et al. | 385/49 |
| 5,439,578 A | 8/1995 | Dovichi et al. | 204/299 |
| 5,498,324 A | 3/1996 | Yeung et al. | 204/452 |
| 5,516,409 A | 5/1996 | Kambara | 204/603 |
| 5,580,471 A | 12/1996 | Fukumoto et al. | 219/121 |
| 5,582,705 A | 12/1996 | Yeung et al. | 204/603 |
| 5,583,736 A | 12/1996 | Anderson et al. | 361/234 |
| 5,710,628 A | 1/1998 | Waterhouse et al. | 356/344 |
| 5,736,410 A | 4/1998 | Zarling et al. | 436/172 |
| 5,784,157 A | * 7/1998 | Gorfinkel et al. | 356/318 |
| 5,867,266 A | 2/1999 | Craighead | 356/344 |
| 5,903,348 A | 5/1999 | Melman et al. | 356/344 |

FOREIGN PATENT DOCUMENTS

| | | |
|---|---|---|
| EP | 0 793 098 A1 | 9/1997 |
| WO | WO 97/45718 | 12/1997 |

OTHER PUBLICATIONS

Taylor, John A. and Yeung, Edquard A., "Multiplexed Fluorescence Detector for Capillary Electrophoreses Using Axial Optical Fiber Illumination", *Anal. Chem* 1993 65:956–960.

Ueno, Kyoll and Yeung, Edward S., "Simultaneous Monitoring of DNA Fragments Separated by Electrophoresis in a Multiplexed Array of 100 Capillaries", *Anal. Chem* 66 (9):1424–1431 (May 1, 1994).

(List continued on next page.)

Primary Examiner—Frank G. Font
Assistant Examiner—Michael Stafira
(74) Attorney, Agent, or Firm—Hamilton, Brooks, Smith & Reynolds, P.C.

(57) ABSTRACT

A system for aligning the optical components of a chemical analysis system in which capillaries or optical fibers are supported by a substrate. The system provides for alignment of elements of an electrophoresis system in an efficient high sampling rate capability. The system provides multiple sources, such as lasers or LEDs that are optically coupled to each capillary or channel. Multi-analyte capability, a variety of analysis modes and DNA sequencing operations are applications of systems using a plurality of lasers per channel.

22 Claims, 13 Drawing Sheets

OTHER PUBLICATIONS

Fung, Elize N. and Yeung, Edward S., "High–Speed DNA Sequencing by Using Mixed Poly (etheylene oxide) Solutions in Uncoated Capillary Columns", *Anal. Chem.* 67 (13):1913–1919 (Jul. 1, 1995).

O'Donnell, Thomas R. "Genetic Reader", The Des Moines Registry, (Jul. 1995).

Yeung et al. "Superfast, Highly Accurate DNA Sequencer to be Commercially Available in 1996", Ames Laboratory (Jul. 1995).

Borman, Stu, "Developers of Novel DNA Sequencer Claim Major Performance Advances", C&EN Washington, (Jul., 24, 1995).

* cited by examiner

Label 1 Signature

Label 2 Signature

Label 3 Signature

Label 1 Signature

Label 2 Signature

Label 3 Signature

Label 4 Signature

SYSTEM AND METHOD FOR MOLECULAR SAMPLE MEASUREMENT

RELATED APPLICATIONS

This application is a divisional of U.S. application Ser. No. 09/345,904 filed on Jul. 1, 1999 now U.S. Pat. No. 6,084,667 which is a continuation-in-part of U.S. application Ser. No. 09/010,031 filed on Jan. 21, 1998 now U.S. Pat. No. 6,084,667 which is a continuation-in-part of U.S. application Ser. No. 08/815,219 filed on Mar. 12, 1997 now U.S. Pat. No. 5,903,348, the entire contents of the above applications being incorporated herein by reference.

BACKGROUND OF THE INVENTION

Capillary Gel Electrophoresis (CGE) is a sensitive method for analysis and identification of biological molecular systems. CGE is a relatively new analytical separation technique that can be applied to the analysis of a wide variety of compounds that provide for improved resolution over other existing techniques. Its use for increasing the rate at which DNA sequencing can be performed has been of particular interest. Because of its sensitivity, the technique is gaining acceptance in many laboratories and manufacturing operations of drug and chemical manufacturers worldwide. However, the instrumentation that is being used to produce the data using this technique is still relatively inefficient, complex and expensive. Although these systems can appear physically different from each other, they all contain the basic functional blocks required for this type of analysis. Each has a method of holding the capillaries, injecting samples therein, transmitting and collecting light, detecting a fluorescent signal from each sample being measured that is induced by the incident light energy, applying voltage to the capillaries, and outputting the collected data in some form.

What these systems generally suffer from is that the techniques involve equipment that is not cost effective for high volume manufacturing, and consequently does not permit widespread use of this important analytical technique. The performance of a single capillary system depends on the method of sample excitation and on the signal collecting optics. In multi-capillary systems precise alignment of delivery, collection and sample assemblies can be difficult. In free beam systems this has been done by visual inspection of reflected or transmitted laser light.

There is a continuing need for improvements in systems for performing optical measurements of biological samples that are readily manufacturable, have low maintenance costs and provide for fast accurate analysis of a large number of samples.

SUMMARY OF THE INVENTION

This invention relates to a system and method for delivering light to chemical or biochemical samples using an aligned optical fiber delivery system that couples light from a light source with an array of sample channels. Light from the samples is collected and detected for data analysis, presentation, and storage. The optical signal collection is accomplished by a second optical fiber system. In a preferred embodiment, the delivery and collection optical fiber systems are mounted and permanently aligned on a mounting structure such that each channel or capillary is in the same plane as the delivery fiber and collection fiber for that capillary. The delivery and collecting fibers can be selected with respect to their core sizes and numerical apertures to satisfy the particular application requirements. The collecting fiber largely filters out the excitation light, reducing the detection noise and improving the detection sensitivity. A multi-mode fiber can be used for this purpose. In an optical fiber CGE delivery and collection system, the collecting fiber fulfills the role of a spatial filter, lens and a light guide. The two fibers and the capillary are co-planar, enabling a practical and inexpensive method of fabricating a multichannel assembly. The spatial filtering of the undesired, noise-generating, excitation light in the collecting fiber has improved performance over free beam systems where reflections dominate the fluorescence signal.

This fiber optical system presents a number of advantages over the free beam technology used in existing systems. There are no optical components other than fibers, thereby reducing cost, complexity and size. Also, the geometry reduces the amount of excitation light reflected back to the collecting fiber, improving signal to noise ratio. Another advantage of this fiber system is simplification of multicolor detection in comparison with free beam optics where the focal length of lenses, or deflection angles are wavelength sensitive, making simultaneous focusing of different colors difficult. This is not the case in a fiber based system where the emitted light fills substantially the same cone of light at the fiber output and input.

A preferred embodiment of the invention pertains to all fiber systems where the fiber and capillary assemblies are fabricated by affixing them on precision planar surfaces. This relies on highly precise features or grooves formed on a silicon wafer or substrate, for example, by well known micromachining techniques. A large number of capillaries can be precisely aligned and measured with this system, thereby substantially increasing the rate of sample analysis. Arrays of capillaries or channels can be manufactured in multiples of 4 or 8, including 16 or 32, for example. Features are accurate to within 10 microns or less to provide the accurate positioning necessary to achieve the desired measurement accuracy.

Another preferred embodiment of the invention relates to the use of the grooves or channels in the substrate instead of the capillary tubes to confine the gel. A quartz window can be attached to the grooved substrate to provide an optical window for all of the channels in an array. The window can also have a groove to provide a symmetric cross-section to the channel.

Alignment features can also be incorporated in the substrates. An optical alignment system is described here where an alignment accuracy of less than 10 microns, and preferably of about 1 um is employed. This method makes use of the precise geometry of the fiber and capillary assembly substrates.

The registration feature can be a single or a multiple groove structure depending on the method used. The optical registration technique involves detecting a change in surface reflectivity when a fiber tip moves over a groove or a similarly reflecting feature in the reflecting surface. If the fiber position is fabricated precisely with the reflecting feature the change of reflectivity indicates the point of registration.

Another preferred embodiment of the invention includes a system and method for positioning an optical fiber relative to a measurement cell such as a capillary tube. In this system light emitted by an optical fiber is reflected by the capillary surface, for example, and the intensity of the sensed reflected signal is compared to a reference value. The comparison is used to stop the motion of the optical fiber system when it is correctly positioned. A feedback control system can be used to automatically position either the optical fiber system, or the capillary system, relative to the other.

Another preferred embodiment of the invention relates to the use of a light source which emits a plurality of wavelengths. For example, a plurality of lasers can provide multiple color excitation. Multiple lasers are optically coupled to each capillary or channel. Thus, multiple lasers feed a single fiber that carries the light to the sample-carrying capillary. Each source can be modulated at a different modulation frequency so that the combined beams contain multiple modulation frequencies. Further, each source can be modulated separately which minimizes cross talk during coherent detection. A single detector can detect multiple emission peaks simultaneously. The detected fluorescence signal generates photocurrent that contains multiple frequencies. The ratio of the amplitudes depends on the fluorescent label excited by the light beam. This embodiment provides a multi-analyte detection capability and expands the use of the system of the present invention to perform a variety of analysis and DNA sequencing operations.

Another preferred embodiment of the invention includes using a light emitting device such as a light emitting diode (LED) as the light source. The LED light source can provide the user with the option of using a variable intensity for each LED. Thus, the intensity of each LED signal can be modulated at a different frequency and detected using an electronic filter for each detected signal that is tuned to the frequency of the corresponding LED. LEDs with different emission wavelengths can be used for different channels to match the absorption bands of different dyes that can be used in the different channels.

In a preferred embodiment, a plurality of semiconductor lasers can be used to irradiate the channels. For certain applications lasers can provide more efficient pumping of the dye and thereby improve sensitivity. For example, III–V semiconductor materials can be used to fabricate a solid state array of lasers emitting in the visible or near infrared range, and preferably between 400–500 nm that are matched to the excitation band of a selected dye. Gallium nitride based lasers emitting at a center line of 417 nm are available for this application, for example. Such a laser array can be optically coupled using a fiber array or with a lens array as described herein. InGaN based lasers can be used at longer wavelengths. Other regions of the visible or near-infrared up to 850 nm can also be used with LEDs or semiconductor lasers based on GaAs or InGaAs.

A preferred method using two or more lasers emitting at different excitation wavelengths to illuminate each capillary. For example, three lasers emitting at three different wavelengths can be used to measure four different labels having different emission peaks. Each capillary in this four color analysis system can have three or four lasers that are optically coupled therewith using the optical systems described herein.

BRIEF DESCRIPTION OF THE DRAWINGS

The foregoing and other objects, features, and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
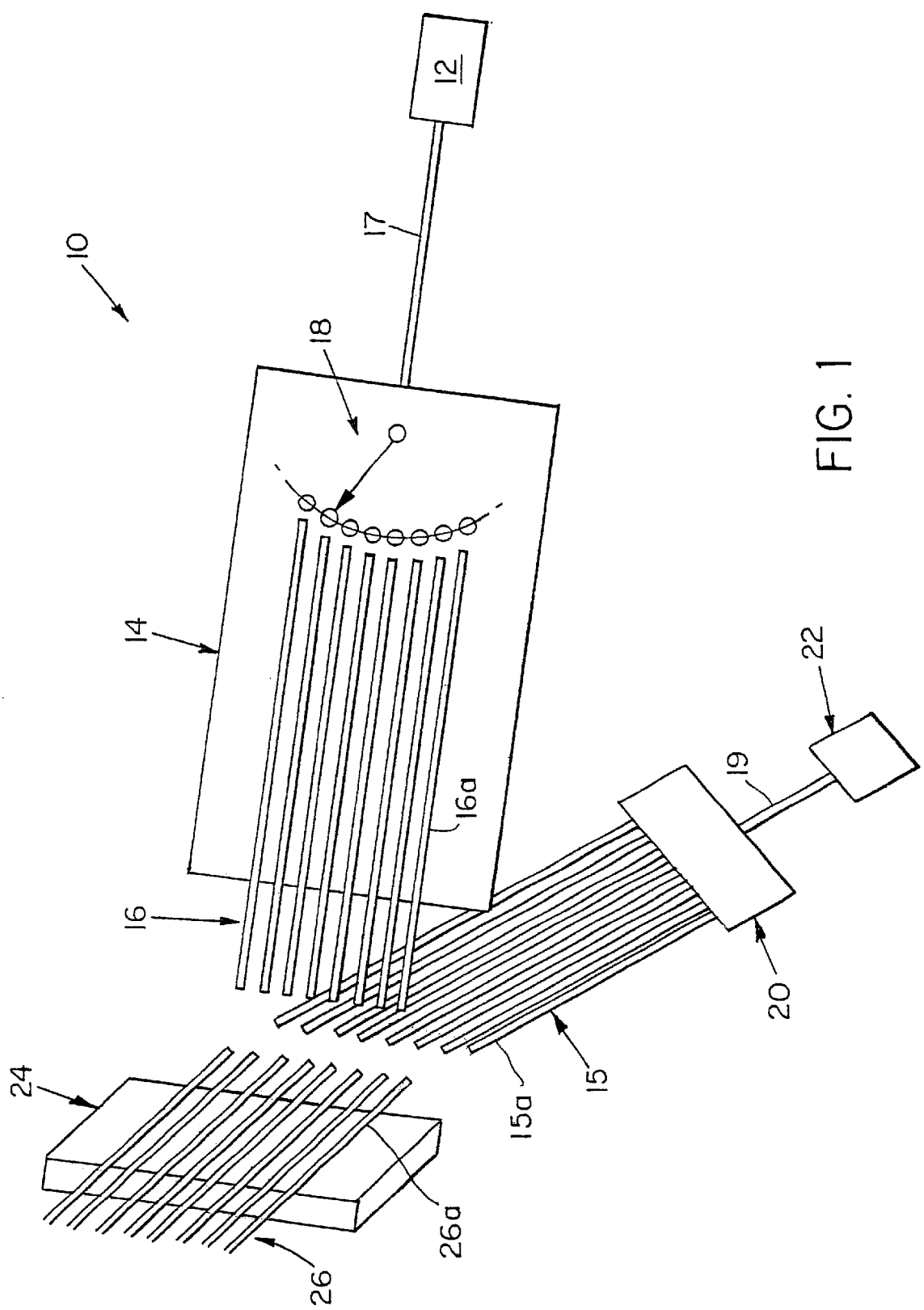
FIG. 1 illustrates a system for optically measuring the contents of a capillary array in accordance with a preferred embodiment of the invention.

A preferred embodiment of the invention is illustrated in the CGE system 10 of FIG. 1. An array of capillaries 26 is provided that are mounted on a first substrate 24. An array of delivery fibers 16 is mounted on a substrate 14 and an optical switch 18 is positioned to couple light from light source 12 to each of the fibers 16 in sequence. Light source 12 can preferably be an argon laser, a solid state laser or any other light source having a suitable emission spectrum for a given application. The light source is coupled to optical switch 18 with a fiber 17. The system also includes an optical combiner or second switch 20 that is coupled to a detector 22 such as a photomultiplier tube or solid state detector device such as a charge coupled device or CMOS detector. As described below the detector is connected to a multichannel analyzer 21, a computer 23 and display 25.

In operation, light from the source is coupled to fibers 16 in sequence. The distal ends of the fibers are each in close proximity to a window on a capillary tube. In a preferred embodiment of the system, each capillary has a corresponding delivery and collection fiber. Each capillary, 26a for example, is in a single plane with its corresponding delivery 16a and collection 5a fiber. This provides a compact system providing for easy alignment.

A mounting structure 150 for the optical fiber system of the present invention is illustrated in connection with FIG. 2. The delivery fibers 16 are mounted onto a precision grooved substrate 14 with an adhesive layer 39. The substrate 14 is mounted onto a mounting element 140 with the fibers extending between the substrate 14 and a first mounting surface of element 140. The collection fibers 15 and second substrate are similarly mounted on a second mounting surface of element 140. The mounting surface define an angle such that the delivery and collection fibers are at an angle between 40° and 50° relative to each other, preferably at about 45°. Smaller angles tend to increase the signal to noise ratio and higher angles tend to tighten the alignment tolerances.

The element 140 can be mounted on a moveable platform or support in which a first actuator 33 and a second actuator 35 can be used to either manually or electromechanically reposition the optical fiber system relative to the capillaries 26. An alignment fiber 29 coupled to a second light source such as a light emitting diode 27 and light sensor 28 can be used for registration. Servo motors can be connected along circuit 37 to computer 23 or other controller to provide for automatic feedback control of the fibers relative to the capillary assembly.

Figure 2:
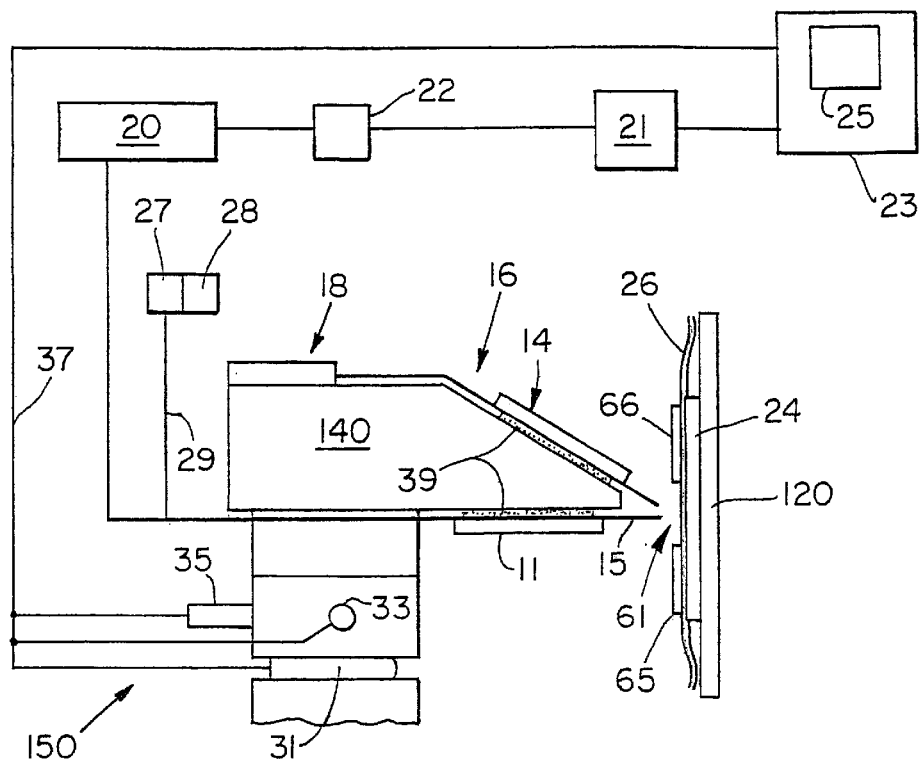
FIG. 2 is a detailed view of the fiber optic delivery and collection system in accordance with the invention.
Figure 3:
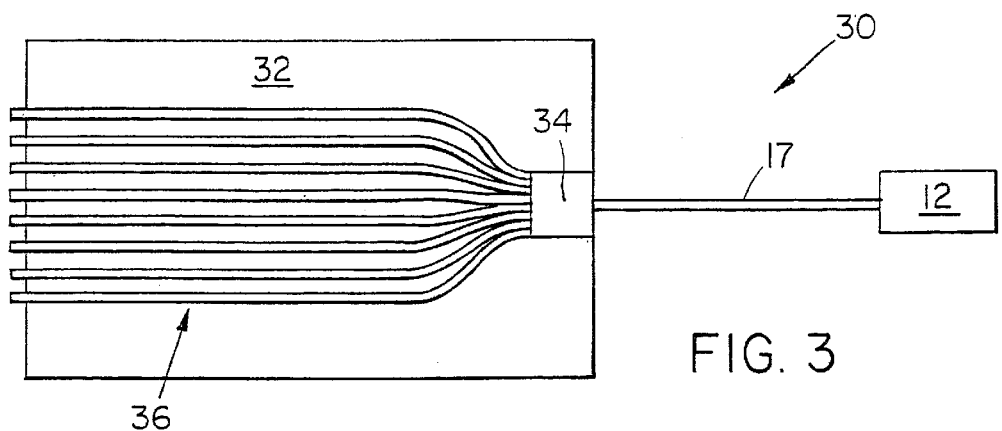
FIG. 3 illustrates an alternative embodiment of the invention using an optical splitter for simultaneous irradiation of capillaries.

In another preferred embodiment the optical switch is replaced by an optical splitter 34 as shown in the illustration of the light delivery system 30 in FIG. 2. In this embodiment, light from the source 12 is delivered through fiber 17 to a splitter, which in the embodiment divides the light into eight separate components and couples the light components into the proximal ends of fibers 36. The fibers 36 are mounted onto the channels of a substrate 32 as described in greater detail below. In this embodiment, although the power requirements for light source 12 are substantially increased, the samples of all eight capillaries that are coupled to the fibers 36 can be measured simultaneously.

A preferred method for fabricating the substrates 14 and 24 is illustrated in connection with the process flow sequence 40 of FIG. 4. In this particular example, a silicon wafer is provided 42 having suitable resistivity, thickness, diameter and crystallographic orientation. The wafer can be cleaned 44 with a mixture of sulfuric acid and water and revised. A masking layer is then deposited 46, preferably a one micron thick layer of silicon nitride using a low pressure chemical vapor deposition process. Next a photolithographic step 48 is performed by depositing and patterning a photoresist to define the channel or groove structure to be formed in the wafer. Note that several patterns can be formed in a single wafer. The linewidths of the resist pattern are then verified and the silicon nitride layer is etched 50 to expose the surface pattern for the grooves in the wafer. The photoresist is then removed and the linewidth of the openings in the silicon nitride layer are measured.

If the pattern is satisfactory, the exposed silicon is etched 52 using a standard etchant, such as a KOH/Alc mixture at 80° C. The remaining silicon nitride can be removed 54 using an HF bath and the wafer surface is rinsed to the desired resistivity.

The grooved silicon substrate can be oxidized 56 to provide an insulting layer having a thickness in the range of 5,000 to 10,000 Angstroms. This can be performed in a thermal oxidation furnace at 950° C.

The wafer or substrate is then diced or cut 58 with a saw to provide a plurality of grooved substrates having desired geometries.

Note that a large number of 8 or 16 groove substrates can be fabricated and affixed to a frame to provide a large number of capillary elements. As many as 96 or more capillaries can be configured in a single system. One or a plurality of lasers can be used depending upon the number of capillaries, the switching capacity and power requirements.

Figure 5:
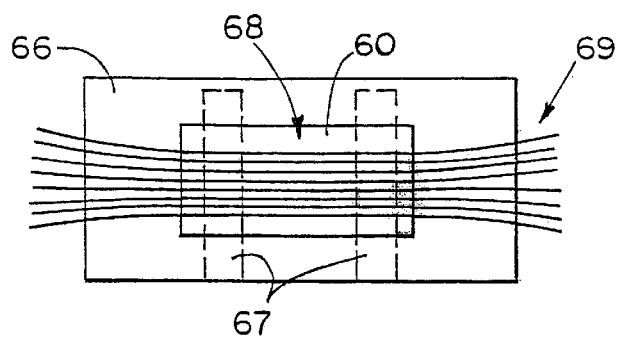
FIG. 5 is a top view of a system for mounting guides onto a channeled substrate in accordance with the invention.

Illustrated in FIG. 5 is an assembly used to mount guides such as optical fibers or capillaries 69 into the channels of a substrate 60. The substrate 60 is held by a vacuum chuck on a supporting surface 66 and two arms 67 are positioned over guides 69 to hold them in the grooves.

An adhesive such as a UV curable commercially available epoxy is placed into the opening 68 between the arms 67 and cured. The arms 67 are then removed and the substrate released from the support 66. This provides a procedure well suited for automated manufacture of registered guide components for optical measurement systems.

Figure 4:
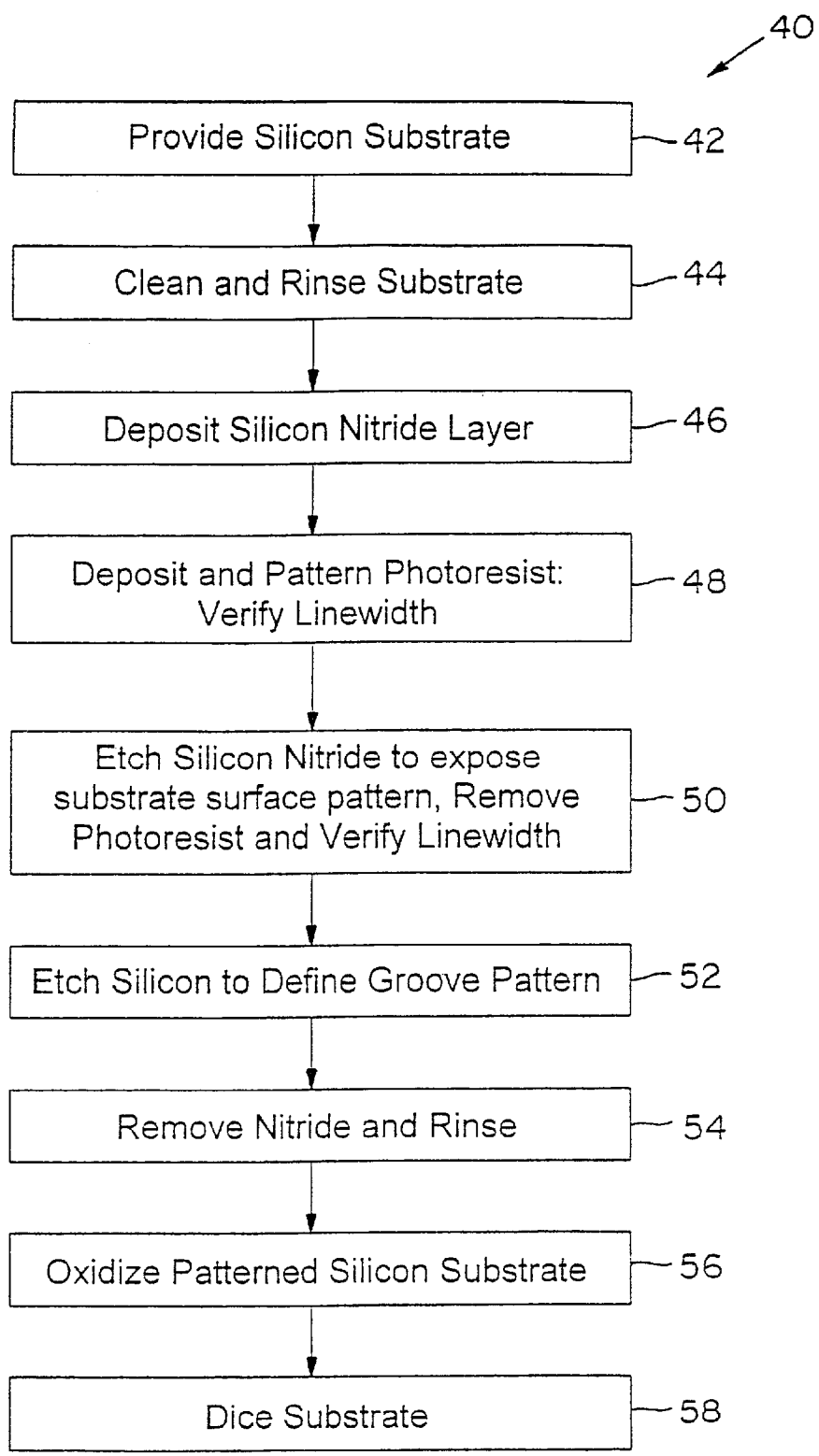
FIG. 4 illustrates a process sequence for making a multi-capillary holder in accordance with a preferred embodiment of the invention.
Figure 6:
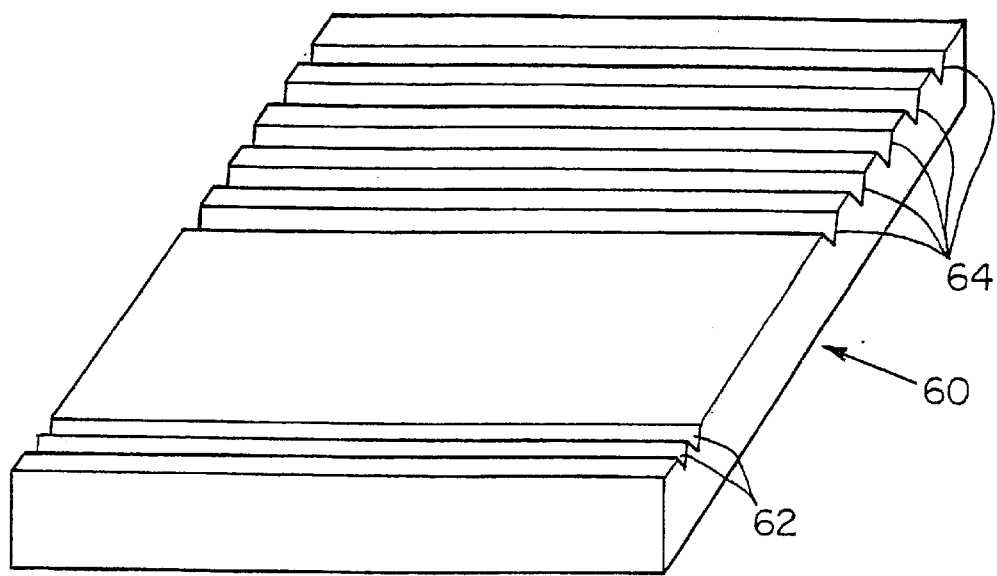
FIG. 6 shows a grooved silicon substrate made in accordance with the method of FIG. 3.
Figure 8A:
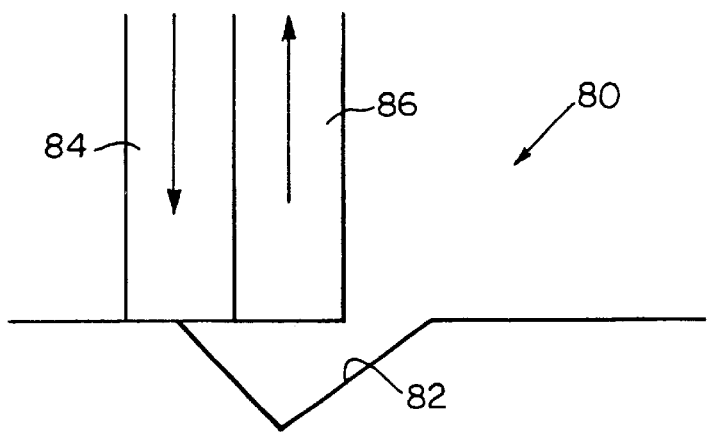
FIGS. 8A and 8B illustrate methods for aligning arrays with a fiber optic device.
Figure 8B:
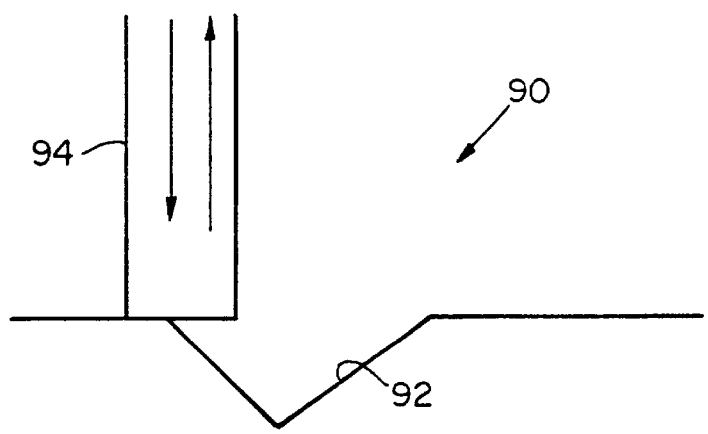

A typical substrate 60 fabricated in accordance with the method of FIG. 4 is illustrated in FIG. 6. The substrate 60 has grooves or channels 64 for holding optical fibers or capillary tubes. Alignment grooves 62 can also be included and used for alignment as shown in FIGS. 8A and 8B below. In another preferred embodiment, the channels 64 themselves can be used to contain the gel. In this embodiment a quartz window can be attached to the grooved surface of substrate 60 to seal the channels and provide an optical window.

Figure 7:
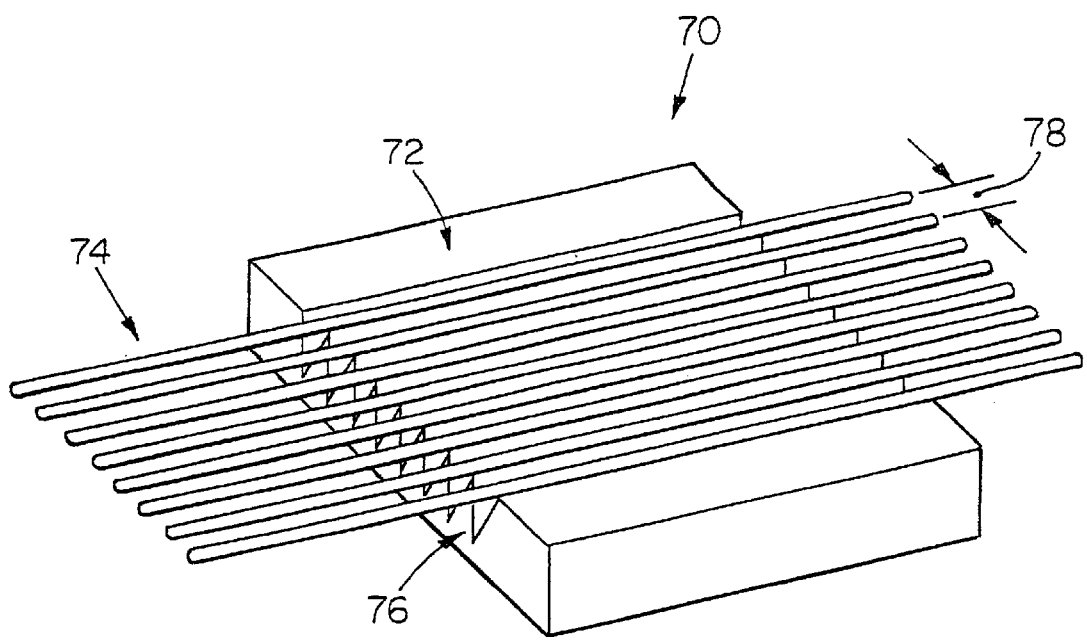
FIG. 7 illustrates an array of capillaries or fibers mounted on a grooved silicon substrate.

FIG. 7 illustrates an alignment module 70 that can be used in the system of FIGS. 1 and 2. The substrate 72 has grooves 76 in which capillary tubes or fibers 74 have been positioned. The distance 78 between adjoining fibers or capillaries is precisely known.

As shown in FIGS. 8A and 8B a two fiber system 80 or single fiber system 90 can be used with a groove 82, 92, respectively, in a substrate to confirm alignment. In system 80 fibers 84 and 86 are used to deliver or collect light from a reflecting feature 82 such as a groove. A detector coupled to the proximal end of fiber 86 will verify alignment. Alternatively, in the single fiber system the reflected signal will null out to indicate a proper registration mark.

Figure 9:
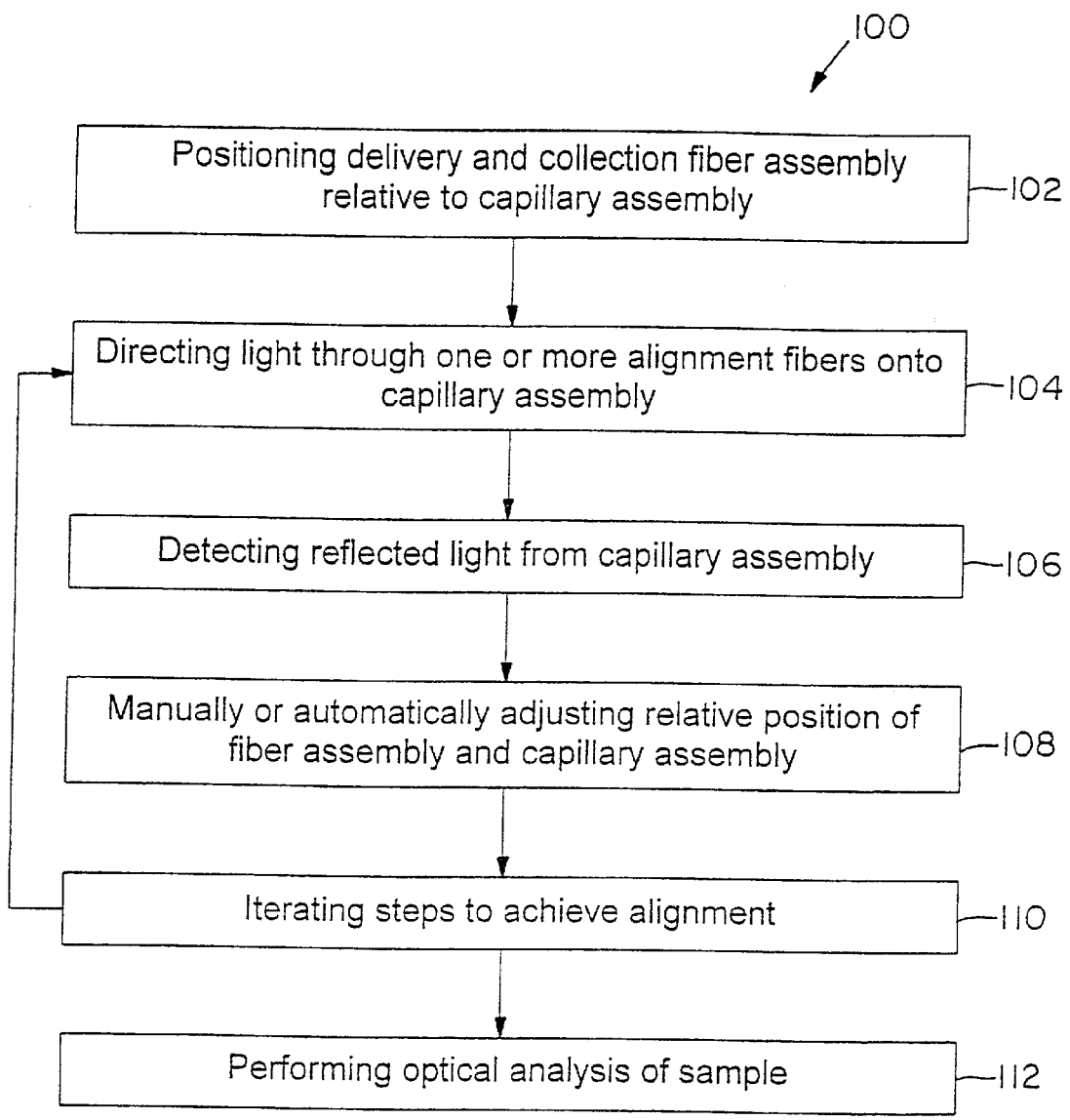
FIG. 9 is a preferred process for aligning the optical elements of an optical analysis system in accordance with the invention.

This process is illustrated in connection with the process sequence of FIG. 9. After initial assembly of the fibers onto element 140 the optical fiber system is positioned 102 relative to the capillaries using visual inspection. Light is directed 104 through one or more alignment fibers onto the capillary assembly and the reflected light is detected 106. Based upon this measurement, the element 140 is repositioned 108 and the light delivery and detection steps are repeated 110 until the capillaries are properly aligned and sample analysis 112 can be performed.

Figure 10:
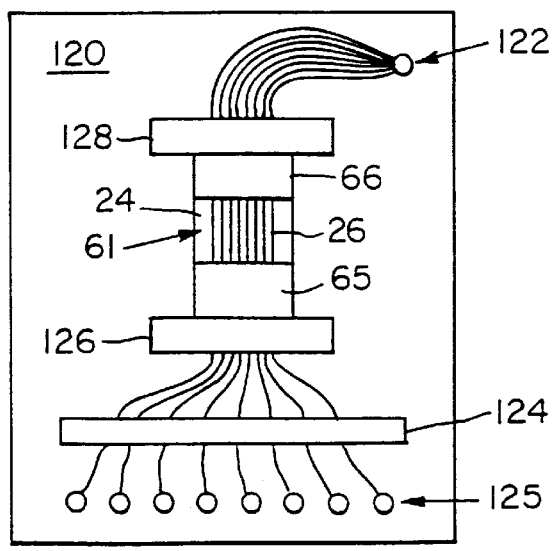
FIG. 10 is a mounting structure for a capillary assembly in accordance with the invention.

Shown in FIG. 10 is a capillary assembly including a support 120, two arms 124 and 128 to hold the capillary substrate onto the support 120, electrical leads 125 to connect to first ends of each capillary, and a capillary holder 124. A common electrical lead 122 can be used to connect the second end of the capillaries to a common electrical connector 122. The capillary assembly can also include silicon panels 65, 66 or the opposite side of the optical fibers relative to substrate 24. The substrate 24 and panels 65, 66 act as a heat sink to remove heat from the capillaries caused by the current passing through them. This prevents thermally induced movement of the capillaries that may result in misalignment relative to the optical fiber system.

Figure 11:
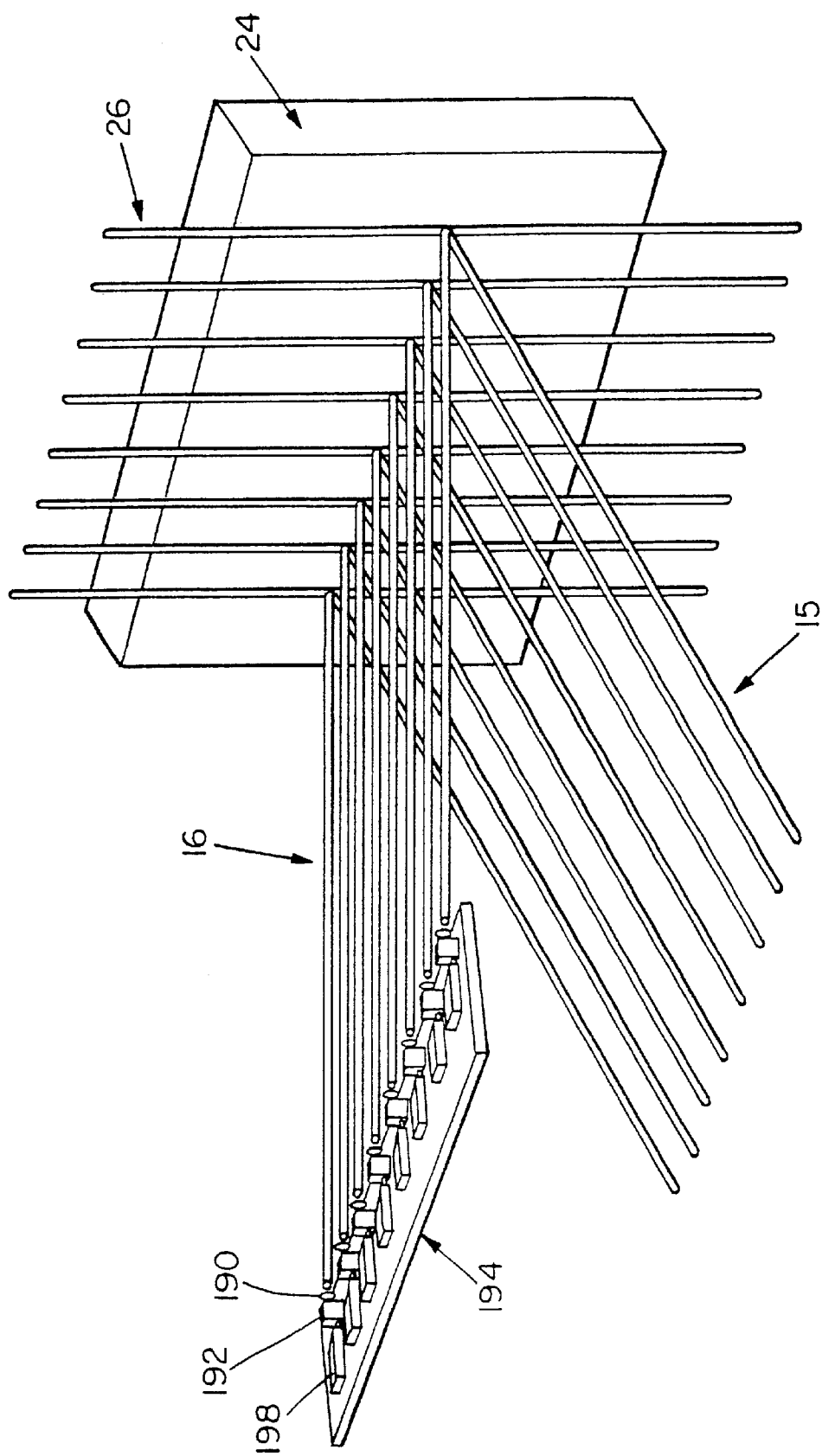
FIG. 11 illustrates a system for optically measuring the contents of a capillary array using a light emitting diode array as the light source.

FIG. 11 shows another preferred embodiment of the invention where the light source is an array of light emitting devices, such as light emitting diodes (LED's). An array of capillaries 26 is provided that are mounted on a first substrate 24. An array of delivery fibers 16 is coupled to an array of LED's 192 by an array of microlenses 190. The array of LED's 192 are attached on a surface of a mounting assembly or module 194 such as printed circuit board. Separate LED drivers 198 are also attached to the mounting assembly 194. A fiber optic collection array 15 is mounted in close proximity to the capillaries 26. In operation, light from the array of LED's is coupled to fibers 16 in sequence. The distal ends of the fibers are each in close proximity to a window on a capillary tube. In a preferred embodiment of the system, each capillary has a corresponding delivery and collection fiber. The LEDs preferably emit light having wavelengths in the range between 430–500 nm. One dye, for example, has an absorption band with a peak of about 495 nm. For this dye, it is preferable to have about 0.6–0.8 mW per channel with a wavelength in the range of 470–500 nm. This provides a substantial reduction in the power needed compared with available lasers where the light is divided into 8 channels, for example. This also eliminates the need for an optical splitter and a modulator or chopper for each channel that are necessary for use with the single laser. As each LED in the array can be driven separately by a compact low cost driver 198, a single controller can actuate each LED in temporal sequence to improve the signal to noise ratio.

Figure 12:
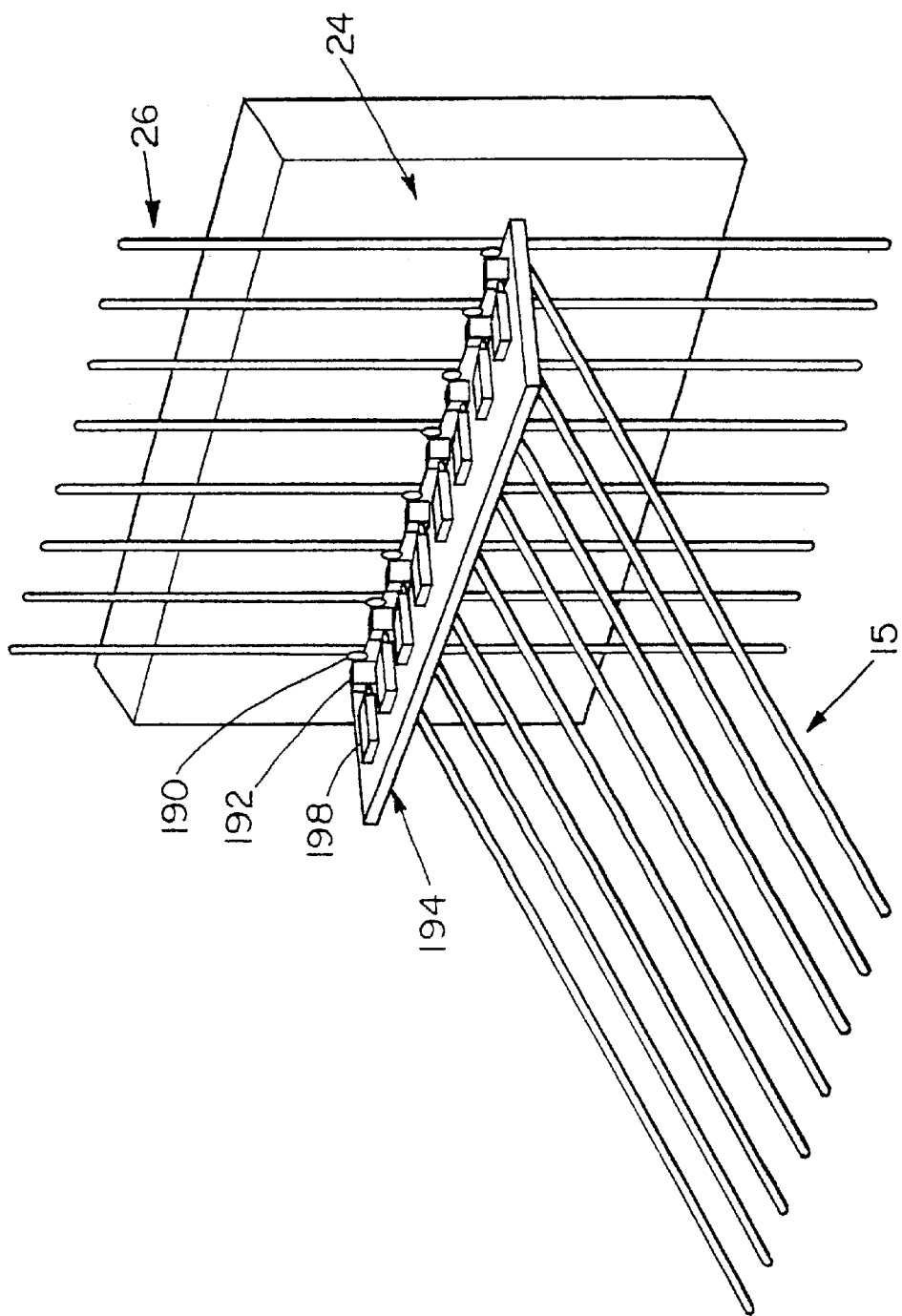
FIG. 12 illustrates another alternative embodiment of a system for optically measuring the contents of a capillary array.

FIG. 12 shows another preferred embodiment of the invention where the LED's 192 are placed in close proximity to the capillaries 26. The array of LED's 192 are attached to the surface of a mounting assembly 194. The array of LED's 192 are optically coupled to the capillaries 26 by means of an array of microlenses 190 which are also attached to the mounting assembly 194. Separate LED drivers are similarly attached to the mounting assembly 194. A controller can also be mounted on the same module 194 to operate the drivers. The controller can be connected to the personal computer 23. The distal ends of a fiber optic collection array 15 is mounted in close proximity to the capillary tubes 26.

Figure 13:
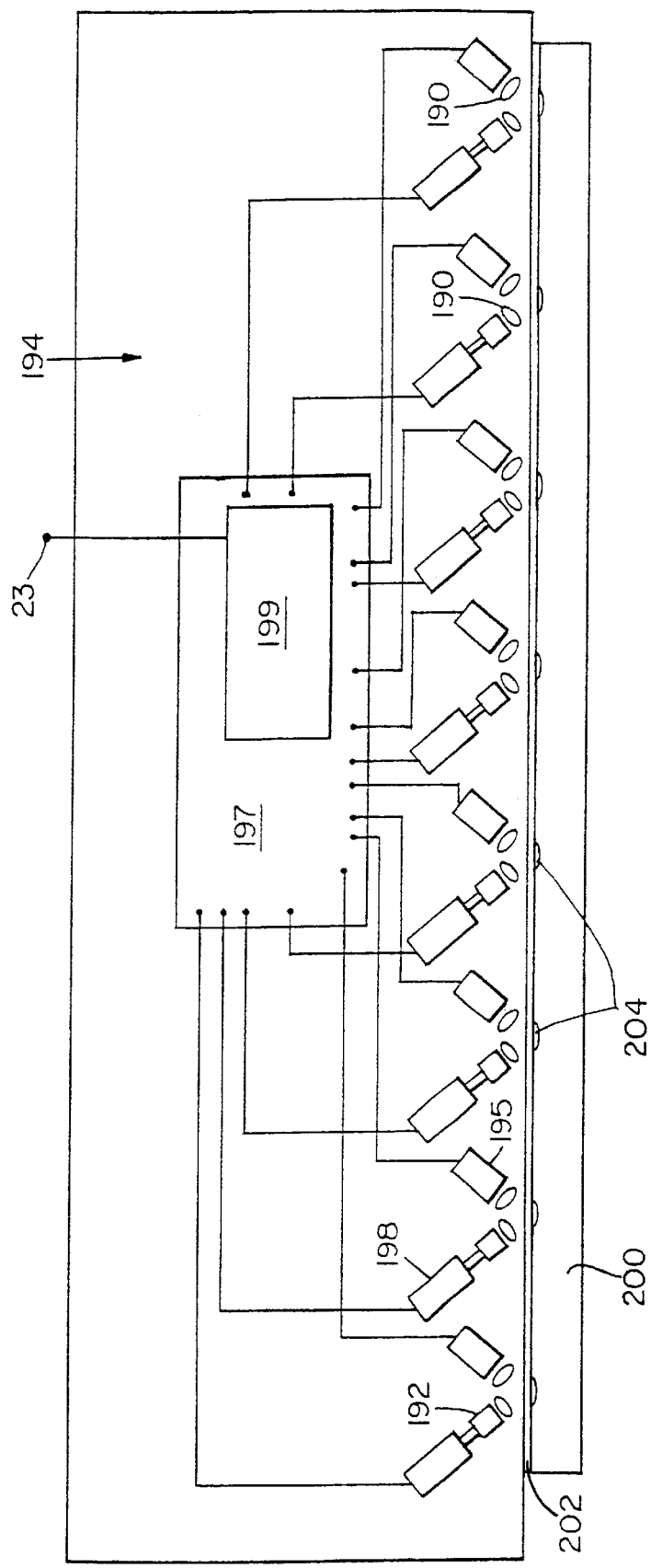
FIG. 13 shows a detailed view of the light emitting diode and detector mounting assembly.

FIG. 13 shows a detailed view of the mounting assembly 194. An array of LED's 192 are attached to the mounting assembly 194. The array of LED's 192 are coupled to an array of LED drivers 198 which are used to independently control each LED 192. An array of microlenses 190, also attached to the mounting assembly 194, is used to couple the array of LED's 192 through window 202 to the array of channels 204 in substrate 200. An array of detectors 195, used to sense any fluorescence in the channels 204 are also attached to the mounting assembly 194. An array of microlenses 190 are also used to couple the detectors 195 to the capillaries. A control processor 197 and an electronic filter 199 are also attached to the mounting assembly 194. The electronic filter 199 is used to limit the frequency range and intensity of the signal that the controller receives from each corresponding detector 195. The filter 199 allows only selected light being amplitude modulated at a certain frequency of the fluorescence of the dye in the channels 204 be received by the computer 23. This prevents any crosstalk or stray emissions from neighboring channels.

Figure 14:
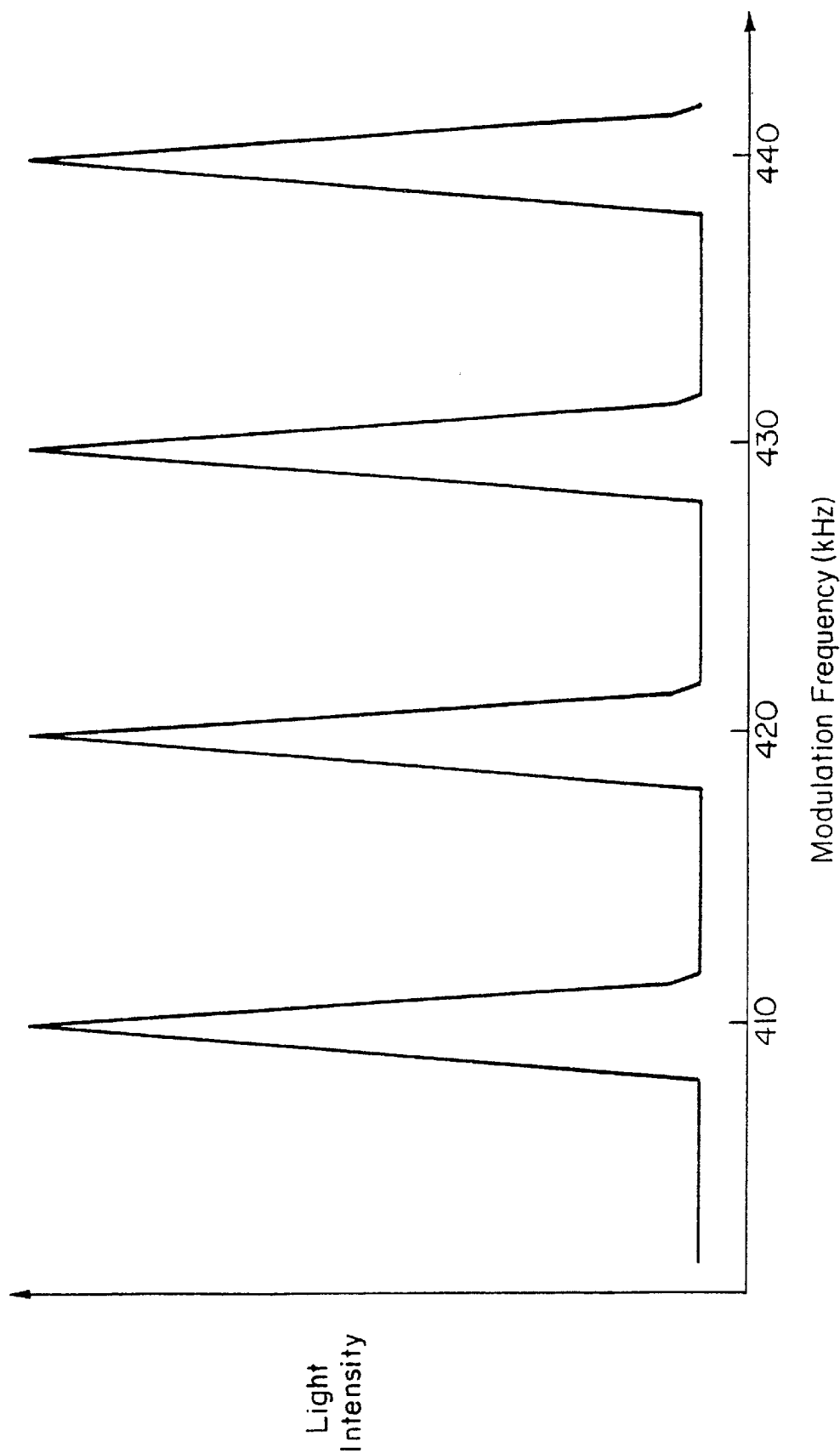
FIG. 14 graphically illustrates the different LED's intensity being modulated at different frequencies.

FIG. 14 shows a graph illustrating the narrow bands at which the intensity of light of four LEDs in an array are filtered. The vertical axis represents light intensity and the horizontal axis represents light modulation frequency. The intensity of the light emitted by each of the LED's in the array can be independently modulated.

In another embodiment of the invention, the light emitting devices 192 are an array of semiconductor lasers, such as gallium nitride or indium gallium nitride, emitting at a wavelength in the range of 400–500 nm. Other semiconductor lasers emitting in the visible or near infrared, for example, gallium arsenide, indium gallium arsenide, aluminum gallium arsenide, indium gallium arsenide phosphide or gallium indium phosphide materials can also be used. Lasers can provide improved sensitivity for certain dyes in which the laser wavelength is well matched to the peak absorption of the dye. A laser array emitting in the range of 700–800 nm, for example, at 780 nm is suitable for certain applications instead of LEDs that can be used in the red portion of the visible spectrum i.e. in the range of 600–700 nm.

Figure 15:
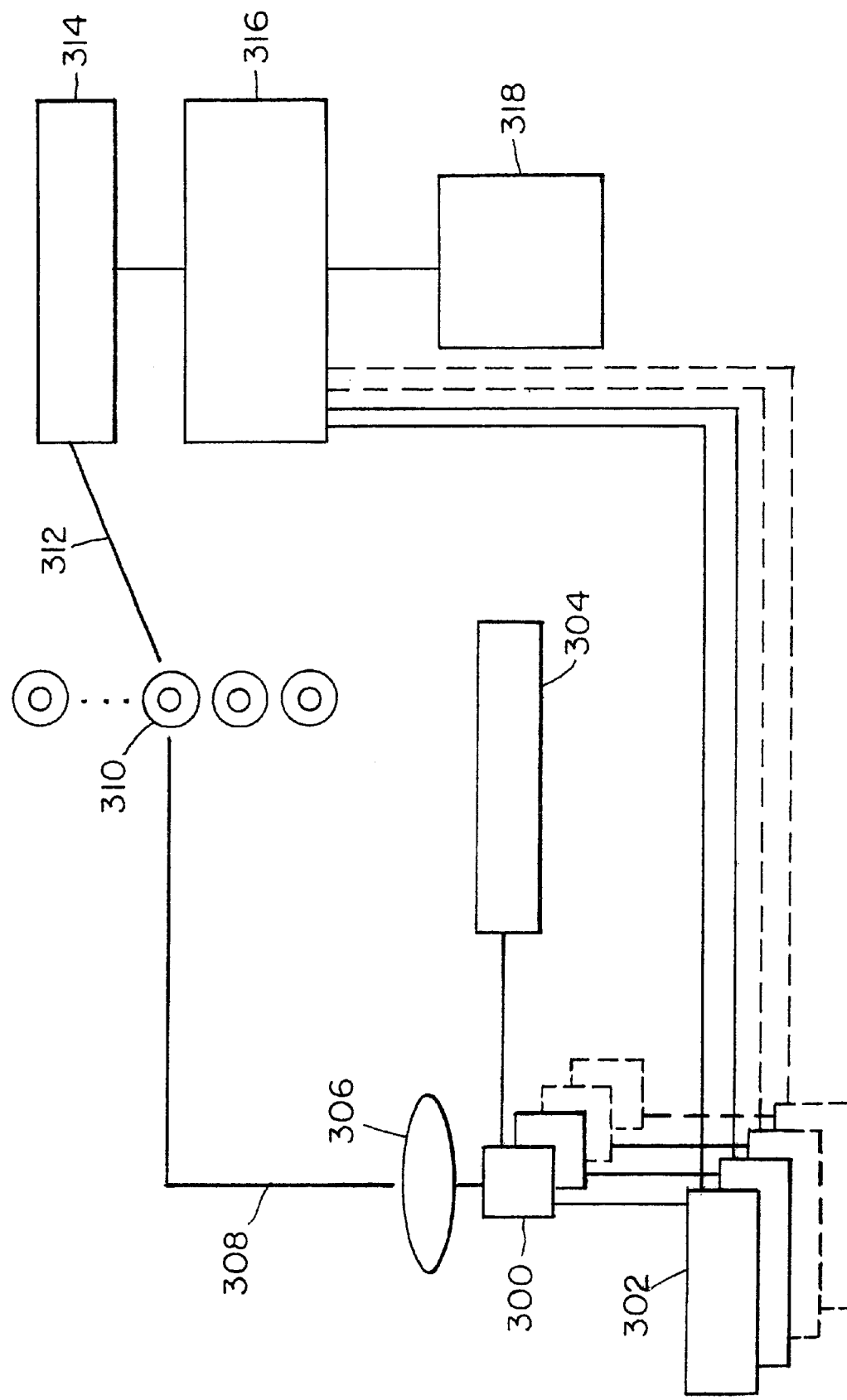
FIG. 15 illustrates an alternative embodiment of a system for optically measuring contents of a capillary array.

FIG. 15 shows another preferred embodiment of the system of the present invention having a plurality of sources emitting at different wavelengths. This embodiment provides a multi-analyte capability, an increased variety of analysis modes and DNA sequencing operations. A plurality of light sources such as semiconductor lasers 300 can be modulated at a different frequency by modulators 302 so that the combined beams contain multiple modulation frequencies. Each modulator 302 is a single frequency generator that supplies an alternating current (AC) at a predetermined single frequency. A current source 304 is coupled to the semiconductor lasers and supplies each laser with a direct current (DC). Thus, each laser 300 is supplied by an AC current from a modulator 302 and a DC current from the current source 304. The output of each laser 300 can be a sinusoidal function. Using a lens system 306, the light emitted from the lasers 300 is optically coupled into a single optical fiber 308. The optical fiber 308, carries light to the sample-carrying capillaries, or capillary 310 as shown in FIG. 15. In a preferred embodiment, each capillary can have a set of a plurality of lasers as it's light source. Thus, the system of a plurality of lasers is replicated for each capillary. The cost of semiconductor lasers is economical to make this a cost effective embodiment. In an alternative embodiment, a splitter can be coupled to the end of the fiber 308 which splits the light emitted from the lasers 300 and provides an optical input into a number of capillaries. The power of the lasers determines how many capillaries can be coupled to the same single optical fiber.

In another preferred embodiment, a line generator is used as opposed to the optical fiber 308. Light from each of the lasers illuminates a region proximal to the input of a plurality of capillaries such as capillary 310. A plurality of capillaries receive light input from the illuminated region. The detected fluorescence signal is collected by the light collection fiber 312. This detected fluorescence signal generates a photocurrent that contains multiple frequencies. The photocurrent is detected by the photodetector 314. The photodetector 314 provides an input into the synchronous detector 316. The synchronous detector 316 detects a signal only if the signal has a frequency that is defined by the modulators 302. The ratio of the amplitudes of the different frequencies contained in the detected fluorescence signal depends on the fluorescent label detected by the light beam. The identification of molecular species translates into the identification of frequency signatures. The synchronous detector can be a single frequency detector including filters. Each filter detects only one frequency that corresponds to a modulator 302 generated frequency.

In the alternative, the synchronous detector is a lock-in amplifier. that is connected to the modulator as shown in FIG. 15. The lock-in amplifier provides a better signal to noise ratio than a frequency detector with filters. The lock-in amplifier detects a signal having the same frequency and phase as the frequency generated by the modulator. A computer 318 can be used to store, display and/or analyze the results of the multi-color, CGE system. In the alternative, referring again to FIG. 1, the light source 12 can emit a plurality of wavelengths.

Figure 16A:
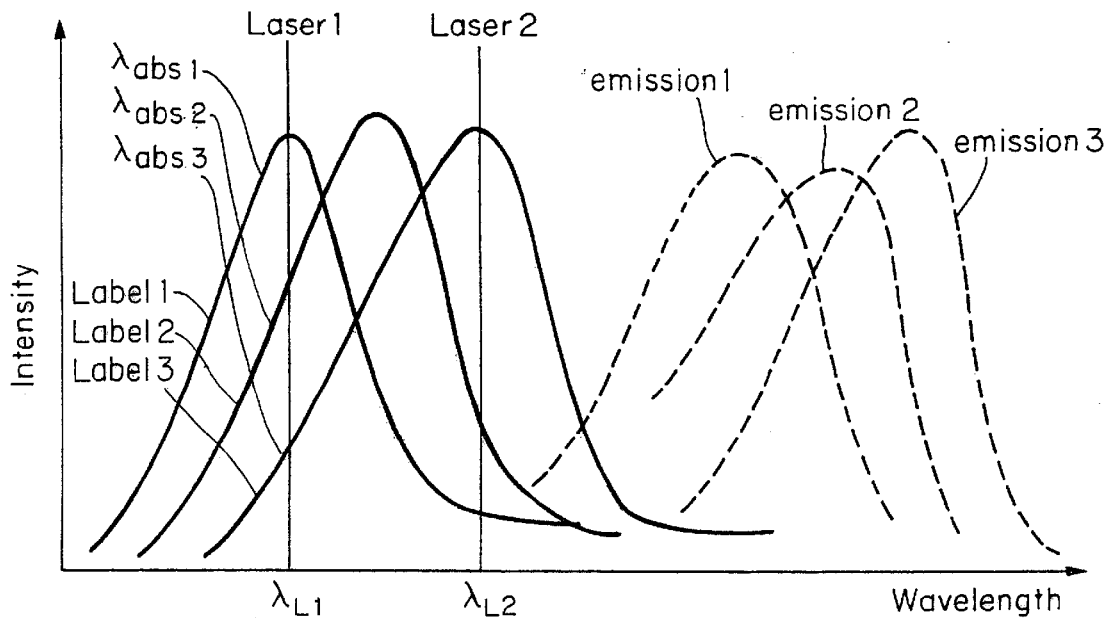
FIGS. 16A–16D graphically illustrate different absorption and emission peaks of three dyes excited by two different lasers, which label different DNA material and the signature of the species detected in accordance with a preferred embodiment of the present invention.

FIG. 16A shows a graph illustrating three different absorption peaks of three dyes which label different DNA bases. The graph further illustrates three different emission peaks which are detected simultaneously by a single detector. A two laser system is used in this preferred embodiment to identify up to three molecular species and can be used for DNA sequencing (with unlabeled fourth base).

Figure 16B:
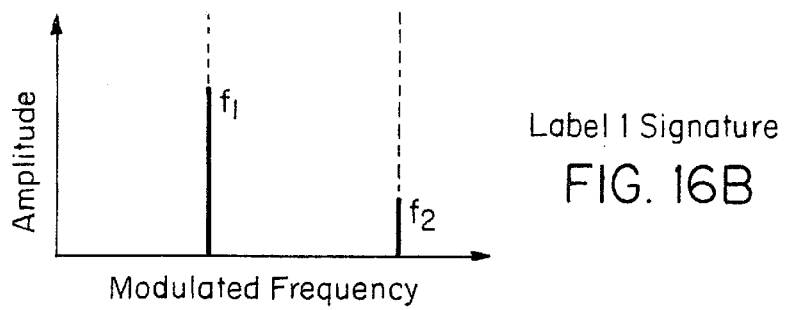
Figure 16C:
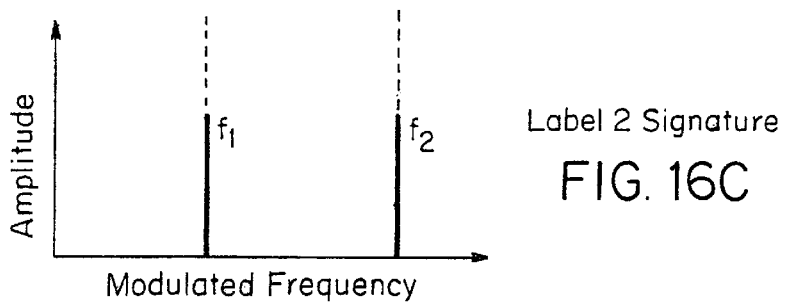
Figure 16D:
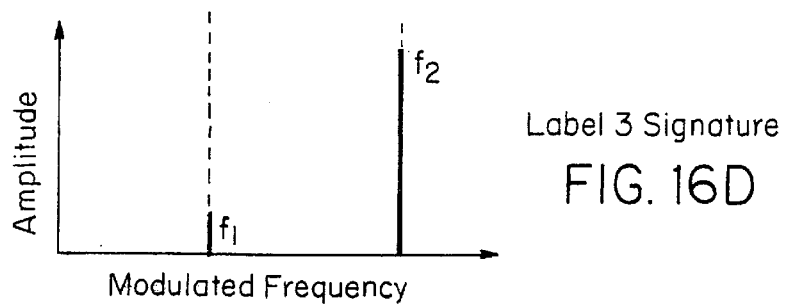

FIGS. 16B–16D graphically illustrate the frequency signature corresponding to the labels. Thus, color of emission is not used for detection of molecular species. The detection optics is simplified by the system of encoding the labels as frequency signatures as well as having a much wider selection of dye labels available.

Figure 17A:
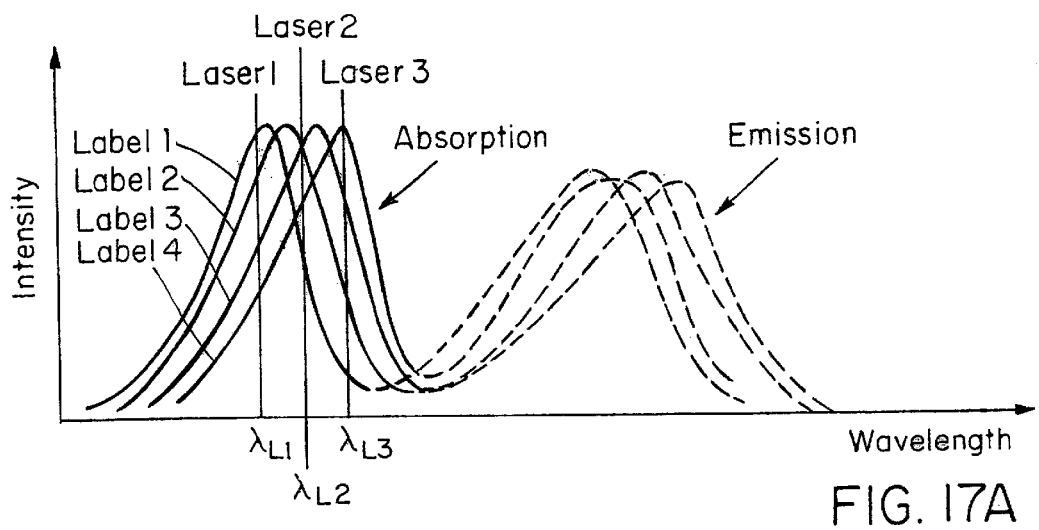
FIGS. 17A–17E graphically illustrate different absorption and emission peaks of four dyes excited by three different lasers, which label different DNA material and the signature of the species detected in accordance with another preferred embodiment of the present invention.
Figure 17B:
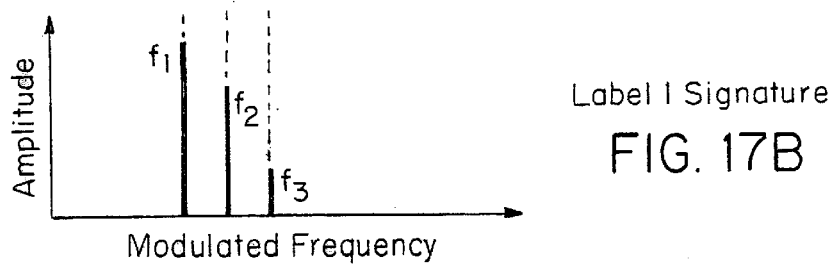
Figure 17C:
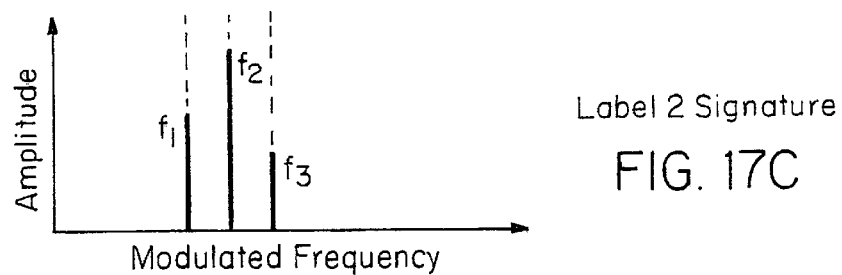
Figure 17D:
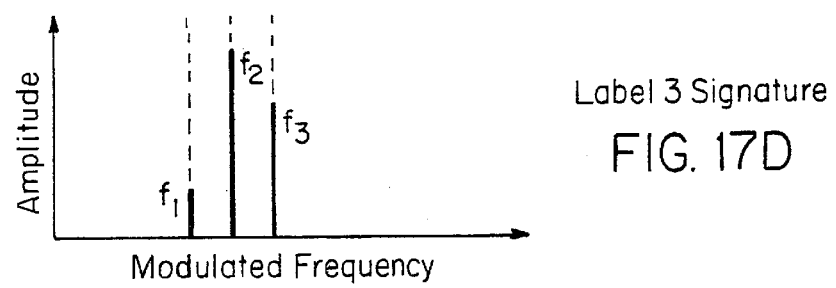
Figure 17E:
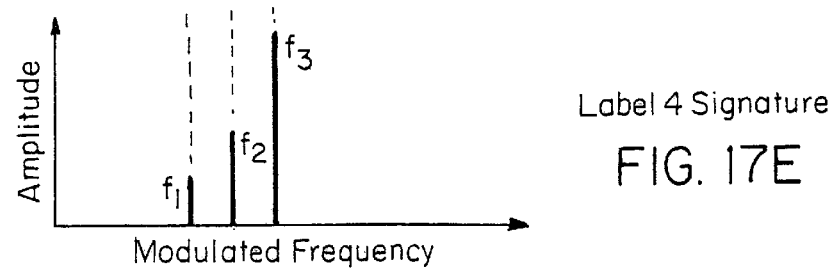

FIG. 17A shows a graph illustrating four different absorption peaks of four dyes which label different DNA bases. The graph further illustrates four different emission peaks which are detected simultaneously by a single detector. A three laser system is used in this preferred embodiment to identify six or more species.

FIGS. 17B–17E graphically illustrate the frequency signature corresponding to the labels. There is a wide selection of lasers within the range of 600 nm to 980 nm that are currently available. Further, recent development of visible and near IR sources has also generated a wide selection of dyes available for labeling. An exemplary tabulation of dyes, such as those supplied by Synthetic Genetics, Inc. of San Diego, Calif. is provided in Table I. Further, Table II lists exemplary Rhodamine dyes that are available for use with the system of the present invention.

TABLE I

| Dye | Color | Absorption Maximum (nm) | Emission Maximum (nm) | Molar Extinction Coefficient $(cm^{-1}M^{-1})$ |
|---|---|---|---|---|
| Dabcyl | — | 453 | None | 32,000 |
| Cy2 | Green | 489 | 506 | 150,000 |
| Fluorescein (FITC) | Green | 494 | 525 | 73,000 |
| FAM(Carboxyfluorescein) | Green | 496 | 516 | 83,000 |
| TET(Tetrachlorofluorescein) | Orange | 521 | 536 | 73,000 |
| HEX(Hexacholrofluorescein) | Pink | 535 | 556 | 73,000 |
| Cy3 | Orange | 550 | 570 | 150,000 |
| TAMRA (Carboxytetramethyl rhodamine) | Rose | 565 | 580 | 89,000 |
| Cy3.5 | Scarlet | 581 | 596 | 150,000 |
| ROX(carboxy-x-rhodaminc) | Red | 575 | 602 | 82,000 |
| Texas Red | Red | 596 | 615 | 85,000 |
| Malachite Green | Green | 630 | None | 76,000 |
| Cy5 | Far Red | 649 | 670 | 250,000 |
| Cy5.5 | Near-IR | 675 | 694 | 250,000 |
| Cy7 | Near-IR | 743 | 767 | 250,000 |
| FluorX | Green | 494 | 520 | 68,000 |

TABLE I-continued

| Dye | Color | Absorption Maximum (nm) | Emission Maximum (nm) | Molar Extinction Coefficient $(cm^{-1}M^{-1})$ |
|---|---|---|---|---|
| Molecular Probes Dyes (all are $200 for 0.2 μmol and $300 for 1.0 μmol-HPLC purification included) | | | | |
| AMCAS | — | 353 | 437 | 19,000 |
| Cascade Blue | Blue | 396 | 410 | 29,000 |
| BODIPY FL | — | 502 | 510 | 82,000 |
| BODIPY 530/550 | — | 534 | 551 | 77,000 |
| BODIPY 493/503 | — | 500 | 509 | 79,000 |
| BODIPY 568/569 | — | 559 | 568 | 97,000 |
| BODIPY 564/570 | — | 563 | 569 | 142,000 |
| BODIPY 576/589 | — | 575 | 588 | 83,000 |
| BODIPY 581/591 | — | 581 | 591 | 136,000 |
| BODIPY FL-X | — | 504 | 510 | 85,000 |
| BODIPY TR-X | — | 588 | 616 | 68,000 |
| BODIPY TMR | — | 544 | 570 | 56,000 |
| BODIPY R6G | — | 528 | 547 | 70,000 |
| BODIPY R6G-X | — | 529 | 547 | 73,000 |
| BODIPY 630/650-X | — | 625 | 640 | 101,000 |
| Marina Blue | Blue | 362 | 459 | 19,000 |
| Oregon Green 500 | Green | 499 | 519 | 78,000 |
| Oregon Green 514 | Green | 506 | 526 | 85,000 |
| Oregon Green 488 | Green | 494 | 517 | 84,000 |
| Pacific Blue | Blue | 416 | 451 | 36,000 |
| Rhodamine Green | Green | 504 | 532 | 78,000 |
| Rhodol Green | Green | 496 | 523 | 63,000 |
| Rhodamine Green - X | Green | 503 | 528 | 74,000 |
| Rhodamine Red - X | Red | 560 | 580 | 129,000 |
| Texas Red - X | Red | 583 | 603 | 135,000 |

| | | $\lambda_{abs}$[nm] | $\lambda_{em}$[nm] | τ[ns] | $\Phi_1$ |
|---|---|---|---|---|---|
| MR200-1 | Ethanol | 620 | 641 | 4.02 | 90 |
| | $H_2O$ | 616 | 636 | 3.62 | — |
| JAS1-DS | Ethanol | 630 | 657 | 3.41 | 54 |
| | $H_2O$ | 628 | 654 | 2.16 | — |
| JA66 | Ethanol | 635 | 659 | 3.89 | 70 |
| | $H_2O$ | 632 | 655 | 2.46 | — |
| JA93 | Ethanol | 667 | 691 | 3.43 | 56 |
| | $H_2O$ | 666 | 687 | 1.79 | — |
| MR116 | Ethanol | 652 | 672 | 2.19 | — |
| | $H_2O$ | 649 | 668 | 1.29 | — |
| MR121 | Ethanol | 650 | 670 | 3.64 | — |
| | $H_2O$ | 662 | 676 | 1.89 | — |

Equivalents

While this invention has been particularly shown and described with reference to preferred embodiments thereof, it will be understood by those skilled in the art that various changes in form and details may be made therein without departing from the spirit and scope of the invention as defined by the appended claims.

We claim:

1. A method of connecting a fiber optic delivery system to a light emitting diode array comprising:

providing a channel flourescence system;

mounting a plurality of light emitting diodes on an assembly;

controlling the light emitted by the light emitting diodes with a driver circuit;

positioning the light emitting diodes relative to an optical fiber delivery system; and optically coupling the light emitting diode array to the optical fiber delivery system with a plurality of lenses.

2. The method of claim 1 further comprising collecting fluorescent light from the channel fluorescence system with an optical fiber collection system.

3. The method of claim 2 further comprising optically coupling a detector to the optical fiber collection system.

4. The method of claim 3 further comprising coupling light from the optical fiber collection system to a plurality of detectors with a plurality of lenses.

5. The method of claim 1 further compriing modulating the light emitted by the light emitting diodes.

6. A method for selecting a bandwidth of detected light in a flourescence detection system comprising:

providing a plurality of capillary channels, each channel being optically coupled to a light source and containing a fluorescence source;

modulating intensity of the light source at a different frequency for each channel;

mounting a fluorescence detector that is optically coupled to a fluorescence source in each channel; and electronically filtering a detected signal to select a bandwidth of fluorescence emitted by the source for each channel.

7. The method of claim 6 further comprising coupling a plurality of light sources to a plurality of channels, each channel containing a fluorescing light source.

8. The method of claim 7 further comprising providing a fiber optic delivery system to couple the light sources to the channels.

9. The method of claim 6 further comprising providing a fiber optic collection system.

10. The method of claim 6 further comprising providing a plurality of fluorescence detectors.

11. The method of claim 6 further comprising providing a light emitting diode light source.

12. The method of claim 6 further comprising providing a semiconductor laser light source.

13. The method of claim 6 further comprising modulating a light source coupled to a channel containing the fluorescence source.

14. A method for synchronous detection of a capillary electrophoresis system comprising:

connecting a plurality of light sources to a plurality of channels using a fiber optic delivery system;

modulating the light sources at different frequencies; and collecting emitted fluorescence from the channels using a fiber optic collection system;

determining ratio of amplitudes of frequencies contained in a detected fluorescence signal.

15. The method of claim 14 further comprising providing a plurality of light emitting diode light sources.

16. The method of claim 14 further comprising providing a plurality of semiconductor laser light sources.

17. The method of claim 14 further comprising providing an electronic controller connected to each of the light sources.

18. The method of claim 14 further comprising providing a plurality of detectors, optically coupled to the fiber optic collection system.

19. The method of claim 6 further comprising providing a plurality of modulators that control a frequency of light emitted by a plurality of light sources.

20. The method of claim 19 comprising providing a lock-in amplifier connected to a modulator to control a frequency and phase of a detected signal.

21. The method of claim 14 further comprising providing a plurality of modulators that modulate the light sources at different frequencies and a plurality of photodetectors connected to electronic filters.

22. The method of claim 14 further comprising providing a plurality of lock-in amplifiers to control a frequency and phase of a detected signal.

* * * * *